United States Patent
Vollmer et al.

(10) Patent No.: US 8,400,639 B2
(45) Date of Patent: Mar. 19, 2013

(54) METHODS AND DEVICES FOR MEASUREMENTS USING PUMP-PROBE SPECTROSCOPY IN HIGH-Q MICROCAVITIES

(75) Inventors: Frank Vollmer, Cambridge, MA (US); Juraj Topolancik, Malden, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 471 days.

(21) Appl. No.: 12/441,159

(22) PCT Filed: Sep. 15, 2007

(86) PCT No.: PCT/US2007/078586
§ 371 (c)(1), (2), (4) Date: Mar. 13, 2009

(87) PCT Pub. No.: WO2008/034118
PCT Pub. Date: Mar. 20, 2008

(65) Prior Publication Data
US 2009/0237666 A1 Sep. 24, 2009

Related U.S. Application Data

(60) Provisional application No. 60/825,771, filed on Sep. 15, 2006.

(51) Int. Cl.
*G01B 9/02* (2006.01)
*G01J 3/45* (2006.01)
(52) U.S. Cl. .................................. 356/480; 356/454
(58) Field of Classification Search .................. 356/432, 356/454, 480, 519; 250/227.19, 227.27; 385/12, 30
See application file for complete search history.

(56) References Cited

U.S. PATENT DOCUMENTS

| | | | |
|---|---|---|---|
| 4,652,120 A * | 3/1987 | Sell | 356/28 |
| 6,765,211 B2 | 7/2004 | Tapalian et al. | |
| 7,082,147 B2 | 7/2006 | Spoonhower et al. | |
| 7,257,279 B2 | 8/2007 | Guo et al. | |
| 2004/0023396 A1* | 2/2004 | Boyd et al. | 435/872 |

OTHER PUBLICATIONS

Topolancik, Juraj et al. "Photoinduced Transformations in Bacteriorhodopsin Membrane Monitored with Optical Microcavities". Biophysical Journal, vol. 92, Mar. 2007, pp. 2223-2229.*

* cited by examiner

*Primary Examiner* — Michael A Lyons
(74) *Attorney, Agent, or Firm* — 24IP Law Group; Timothy R. DeWitt

(57) ABSTRACT

The use of optical microcavities, high-Q resonators and slow-light structures as tools for detecting molecules and probing conformations and measuring polarizability and anisotropy of molecules and molecular assemblies using a pump-probe approach is described. Resonances are excited simultaneously or sequentially with pump and probe beams coupled to the same microcavity, so that a pump beam wavelength can be chosen to interact with molecules adsorbed to the microcavity surface, whereas a probe beam wavelength can be chosen to non-invasively measure pump-induced perturbations. The induced perturbations are manifest due to changes of resonance conditions and measured from changes in transfer characteristics or from changes of the scattering spectra of a microcavity-waveguide system. The perturbations induced by the pump beam may be due to polarizability changes, changes in molecular conformation, breakage or formation of chemical bonds, triggering of excited states, and formation of new chemical species.

20 Claims, 9 Drawing Sheets

METHODS AND DEVICES FOR MEASUREMENTS USING PUMP-PROBE SPECTROSCOPY IN HIGH-Q MICROCAVITIES

CROSS-REFERENCE TO RELATED APPLICATIONS

The present application claims the benefit of the filing date of U.S. Provisional Patent Application Ser. No. 60/825,771 filed by inventors Frank Vollmer and Juraj Topolancik on Sep. 15, 2006, entitled "Methods And Devices For Measurements Of Optical Anisotropy, Molecular Orientation And Polarizability Using Pump-Probe Spectroscopy In High-Q Microcavities," which is hereby incorporated herein in its entirety.

STATEMENT REGARDING FEDERALLY SPONSORED RESEARCH OR DEVELOPMENT

None.

BACKGROUND OF THE INVENTION

1. Field of the Invention

The present invention comprises devices and methods that use optical microcavities as a spectroscopic tool for detecting molecules and for probing conformations and orientations of molecules and molecular assemblies.

2. Brief Description of the Related Art

Optical microresonators with small modal volumes and high quality (Q) factors significantly enhance interaction of the optical field with the material through recirculation, which makes them exceptionally sensitive to the optical properties of the resonator and the surrounding medium. (See, for example, Spillane, S. M., T. J. Kippenberg, and K. J. Vahala, "Ultralow-threshold Raman laser using a spherical dielectric microcavity," Nature 415:621-623 (2002); V. R. Almeida, C. A. Barrios, R. R. Panepucci, M. Lipson, "All-optical control of light on a silicon chip," Nature 431, 1081-1084 (2004); V. S. Ilchenko, A. A. Savchenkov, A. B. Matsko, L. Maleki, "Nonlinear optics and crystalline whispering gallery mode cavities," Phys. Rev. Lett. 92:043903 (2004); and E. Krioukov, D. J. W. Klunder, A. Driessen, J. Greve, C. Otto, "Sensor based on an integrated optical microcavity," Opt. Lett. 27, 512 (2002).)

Exploiting this attribute, optical microcavities have been used successfully for ultra-sensitive detection of heavy water and biomolecules. (See A. M. Armani, K. J. Vahala, "Heavy water detection using ultra-high-Q microcavities," Opt. Lett. 31:1896-1898 (2006); F. Vollmer, D. Braun, A. Libchaber, M. Khoshsima, I. Teraoka, S. Arnold, "Protein detection by optical shift of a resonant microcavity," Appl. Phys. Lett. 80:4057-4059 (2002); F. Vollmer, S. Arnold, D. Braun, I. Teraoka, A. Libchaber, "Multiplexed DNA quantification by spectroscopic shift of two microsphere cavities," Biophys. J. 85:1974-1979 (2003); M. Noto, F. Vollmer, D. Keng, I. Teraoka, S. Arnold, "Nanolayer characterization through wavelength multiplexing of a microsphere resonator," Opt. Lett. 30, 510 (2005).) In biosensing, the sensitivity of microcavities surpasses that of surface-plasmon resonance (SPR) which is widely recognized as the state-of-the-art label-free detection technique. Binding of only a few molecules on the microcavity surface shifts the frequencies of the resonant modes that evanescently interact with the adsorbed material. Monitoring of the shift induced by polarizability or refractive index changes forms the basis of label-free, non-invasive, real-time biodetection and nanolayer characterization. The present invention extends this sensitive technique using devices and methods for pump-probe spectroscopy in high-Q microcavities which can be used to detect molecules and to track dynamic changes in the molecular structure.

Coupled plasmon-waveguide resonance (CPWR) spectroscopy has been developed to probe anisotropies in biological membranes immobilized onto solid surfaces by incorporating a TM- (transverse magnetic) polarized probe in addition to the TE- (transverse electric) polarized one used in conventional SPR. (See Z. Salamon, H. A. Macleod, G. Tollin, "Coupled plasmon-waveguide resonators: A new spectroscopic tool for probing proteolipid film structure and properties," Biophys. J. 73: 2791-2797 (1997).) High-Q optical microcavities represent an interesting alternative to SPR-based techniques providing exceptional sensitivity and two possible probing polarizations and operation at arbitrary wavelengths.

The magnitude of the polarizability changes (A) that accompany structural transformations in, e.g., complex proteolipid macromolecules, is not known, although conformational changes in such systems have been observed qualitatively by CPWR or indirectly by Stark spectroscopy. Given their superior sensitivity and the ability to directly quantify $\Delta\alpha$, the microresonators represent a new quantitative tool for probing molecular transformations in important proteolipid biomolecular assemblies such as G-protein-coupled receptors or in signaling molecules such as calmodulin and disease-related prion proteins. As disclosed herein for the model case of Bacteriorhodopsin (bR), the present invention is particularly suited for pump-probe studies of photosensitive biomolecules. Further examples of such systems include photosynthetic membranes and photoreceptors such as photoactive yellow protein. Further improvements of the microresonator technique promise single-molecule sensitivity which is beyond the scope of any alternative label-free technique. (See S. Arnold, M. Khoshsima, I. Teraoka, S. Holler, F. Vollmer, "Shift of whispering-gallery modes in microspheres by protein adsorption," Opt. Lett. 28:272-274 (2003).) For such applications, a pump-probe approach, where a probe as well as a pump beam excites a cavity resonance, provides added sensitivity for detection of single particles and molecules since absorption of a pump-beam by molecules/particles generates heat, the effect of which can be measured with a probe due to thermally induced refractive index changes. The thermo-optic effect has been demonstrated in toroidal microcavities utilizing only one beam at resonance with a microcavity (A. M. Armani*, R. P. Kulkarni, S. E. Fraser, R. C. Flagan, K. J. Vahala "Label-free, single-molecule detection with optical microcavities" Science, Volume 317, 5839, August 2007). The present invention utilizes a pump probe approach where the resonance wavelength of the pump beam can be chosen deliberately to maximize absorption by molecular analytes and particles. Although high circulating power is advantageous, the resonance excited by the pump beam does not have to be associated with a high-Q factor, since sensitive detection is achieved with a probe beam that (simultaneously or sequentially) excites a high-Q resonance in the same microcavity. The resonance wavelength of the probe beam is chosen to maximize Q-factor and thus sensitivity for detection.

SUMMARY OF THE INVENTION

The present invention comprises devices and methods that use optical microcavities as a spectroscopic tool for detecting molecules as well as probing conformations and orientations of molecules and molecular assemblies. The approach is based on the use of a pump beam and a probe beam which both excite resonance in the same optical microcavity where coupling can be achieved through one or more waveguides (FIG. 1). Different light sources 160 (e.g. tunable lasers) are coupled to the waveguide 170 for this purpose. Intensity and polarization for each wavelength can be controlled independently using combinations of in-line polarizers 130, couplers 140, and waveplates 150. Transmission of the microcavity-waveguide system is measured using a photodetector coupled 190 to a waveguide 170, or a photodetector 180 is used to collect the light 182 scattered from the microcavity 120. The pump beam interferes with molecules adsorbed on the microcavity and can e.g. be used to trigger conformational changes, break/form chemical bonds, induce excited states, excite vibrational and rotational molecular modes, induce/prevent chemical reactions or generate heat by absorption. Simultaneously or sequentially, a probe beam non-invasively (meaning without triggering a similar response in the adsorbed molecules) measures such perturbations. This is possible since a change in molecular conformation, breakage/reformation of chemical bonds, polarizability, heat generation etc. induced by the pump will change the resonance condition 122 for the probe beam and thus the transfer characteristics of the waveguide-coupled microcavity system. This can be measured for example by tracking a resonance 124 in a transmission spectrum obtained by scanning a coherent source (probe). Alternatively, one can measure directly the change in transmitted probe intensity of the waveguide-coupled microcavity system using a photodetector 190 coupled to the output waveguide or using a photodetector 180 that collects the light scattered from the microcavity (FIG. 1). In some embodiments which are used for detection of conformation and orientation of molecules, the use of transverse electric (TE) and -magnetic (TM) polarized resonant modes (or in general modes with different spatial field distribution/states of polarization) extends sensing capabilities of microcavities by allowing anisotropy measurements, measurement of molecular orientation, and measurement of the orientation of the transition dipole moment (FIG. 2). In this context, proteolipid membranes (e.g. Bacteriorhodopsin, FIG. 3) are a particularly relevant subject for investigations as they are central to many areas of life sciences and are difficult to study with alternative optical techniques such as surface plasmon resonance (SPR) since in conventional SPR only TE polarized modes can be excited in the thin gold film and their use is limited to the visible. The orientation of a transition dipole moment can be determined by exciting the molecule 210 using the pump beam at different polarization (e.g. TE or TM). The orientation of a molecular assembly can be determined by probing the perturbed (pump) or unperturbed molecule using the probe at different polarization (TE or TM).

The present invention is also based on operation of microcavities at arbitrary, e.g. visible and near-infrared (near-IR), wavelengths which is particularly important for non-invasive sensing with photosynthetic- or bacterial membranes that contain light-absorbing chromophores. The operation at arbitrary wavelengths is particularly important for non-invasive sensing because an optical probe could trigger molecular transitions in binding macromolecules, which would interfere with the analysis. This is the case for example with photosynthetic pigments (see S. G. Boxer, Stark Spectroscopy of Photosynthetic Systems (Academic Publishers, The Netherlands, 1996) or Rhodopsins (see R. R. Birge, Annu. Rev. Phys. Chem. 41, 683 (1990)) that contain light-absorbing chromophores in the membrane. We disclose that anisotropies of such systems can be probed with high-Q microresonators using polarized modes at wavelengths far from any molecular absorption, e.g., in the near-IR. Furthermore, a pump-probe spectroscopy can be implemented where an optical pump centered at the molecular resonance (absorption band) induces structural changes which are then dynamically monitored off-molecular-resonance with a probe. The approach is demonstrated by way of example by measuring photoinduced conformational changes in the biological photochrome bacteriorhodopsin (bR, FIG. 3). bR is ideal for such a demonstration since its structure is well known, it self-assembles easily onto a silica surface (see J.-A. He, L. Samuelson, L. Li, J. Kumar, S. K. Tripathy, Adv. Mater. 11, 435 (1999); J.-A. He, L. Samuelson, L. Li, J. Kumar, S. K. Tripathy, Langmuir 14, 1674 (1998)) and its molecular conformation can be switched optically between two stable states (see B. L. Fering a, Ed., Molecular Switches (Wiley-VCH GmbH, Weinheim, Germany, 2001)). A model study of the photoinduced all-trans to 13-cis isomerization of the chromophore retinal in bR by monitoring the shift of polarized whispering-gallery modes (WGMs) in the near-IR is described. Further, a method is described to quantitatively analyze the associated molecular polarizability changes which show that the shift ratio for the two polarizations (TE/TM) reflects the orientation of the retinal with respect to the microsphere surface. Limitations and possible applications of the introduced spectroscopic technique are additionally discussed.

In a preferred embodiment, the present invention is an optical device that comprises a high-Q resonant or slow light structure and one of an interface, a surface or a mode volume accessible for interactions with a sample 110. Resonant or waveguide modes are excited in said high-Q or slow light structure at none, one or more pump wavelengths and at one or more probe wavelengths, and the resonant modes are excited simultaneously or sequentially. The high Q structure may comprise at least one selected from the group of: microspherical cavities, microtoroidal cavities, microring-cavities, microdisk cavities, photonic crystal defect cavities, disordered photonic crystal waveguides, fabry-perot cavities, and photonic crystal waveguides. The resonant or waveguide modes may be linearly (e.g. transverse electric or transverse magnetic) or circularly polarized. Further, the resonant modes are excited by one of evanescent coupling from an optical waveguide, evanescent coupling from a photonic crystal waveguide, evanescent coupling from a tapered optical fiber, an evanescent coupling from a tapered optical fiber tip and a free-space beam. Further, the resonant modes or waveguide modes may be excited using at least one selected from the group of: distributed feedback laser, an external cavity laser, an organic dye laser, surface emitting laser diodes, quantum dot emitters. A wavelength (frequency) of a resonant mode is detected from spectral features of a transmission or scattering spectra recorded with photodiodes in a spectral regions. Transfer characteristics of the high Q structure may be determined from intensity measurements of transmitted or scattered light recorded with photodiodes in one or more spectral regions. A photodiode may be connected to a waveguide that connects to the high-Q or slow light structure. The photodiode collects scattered light from the high-Q or slow light structure. The resonant mode is excited at two or more wavelengths simultaneously or sequentially.

The sample may be delivered to the interface, surface or mode volume using pressure operated microfluidic channels or microfluidic channels operated by electrophoresis or die-electrophoresis. The sample may self assemble on the said interface or surface. The sample may comprise one of a liquid, a gas, a molecular monolayer, a self-assembled monolayer, an ultra-thin film, un-specifically adsorbed protein molecules, un-specifically adsorbed DNA molecules, specifically bound protein molecules, specifically bound DNA molecules, small organic molecules, antibodies, single molecule. Further, the sample may comprise one of an optically anisotropic component, a biological membrane such as photosynthetic membranes or rhodopsin containing bacterial membranes, a photochromic protein such as photoactive yellow protein or green/yellow fluorescent protein, a prion proteins, a signaling molecule such as calmodulin, a protein with one of photoactive yellow protein, green fluorescent protein or yellow fluorescent protein as a component, one or more photochromic compounds.

Still other aspects, features, and advantages of the present invention are readily apparent from the following detailed description, simply by illustrating a preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description, or may be learned by practice of the invention.

BRIEF DESCRIPTION OF THE DRAWINGS

For a more complete understanding of the present invention and the advantages thereof, reference is now made to the following description and the accompanying drawings, in which.

DETAILED DESCRIPTION OF THE PREFERRED EMBODIMENTS

In a preferred embodiment of the present invention, optical microcavities are used as a sensitive spectroscopic tool for detecting molecules and probing conformations and orientations of molecular assemblies. An exemplary setup and exemplary methods are described for measurements of photoinduced conformational changes in bacteriorhodopsin membrane.

Figure 1:
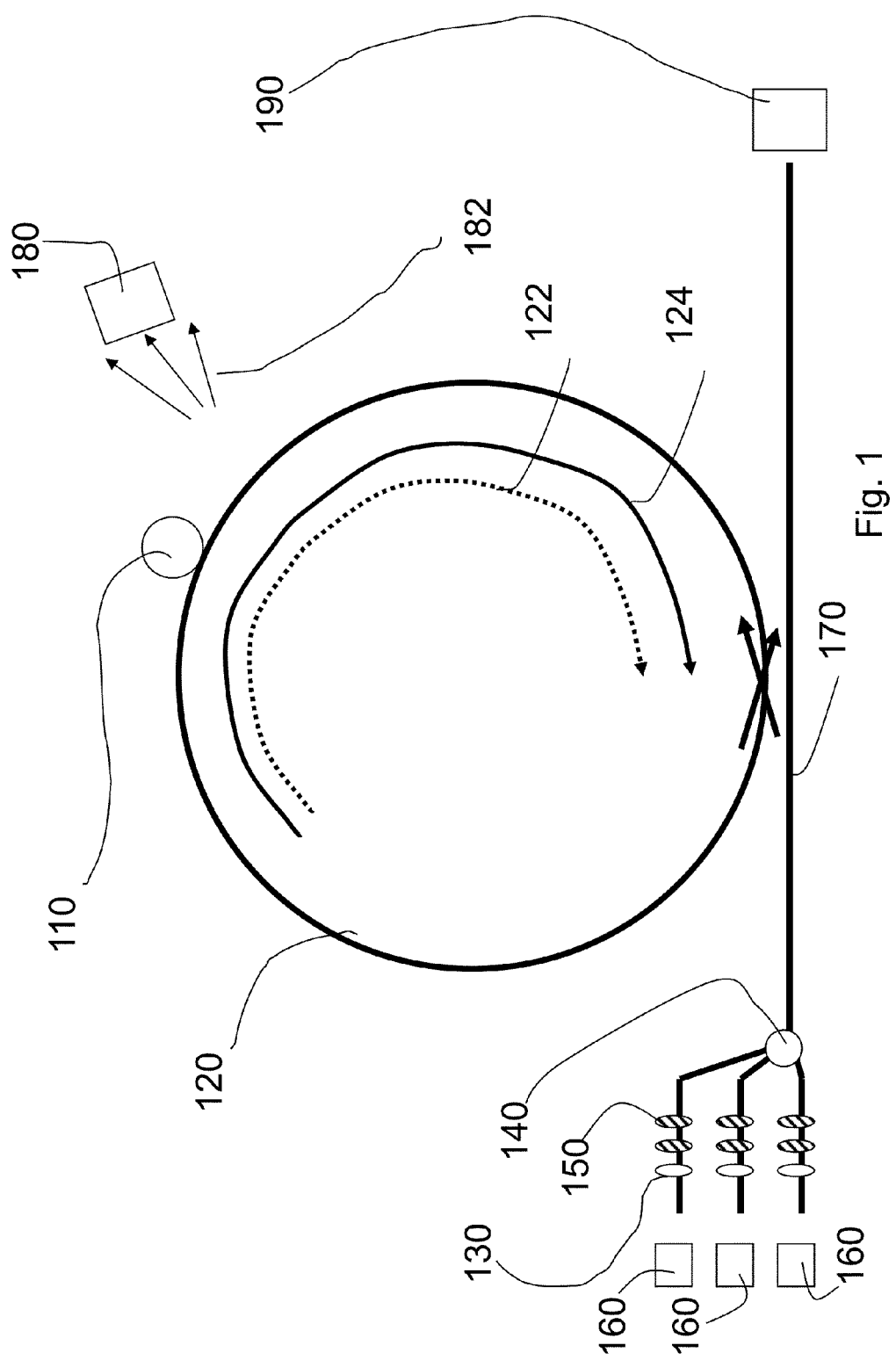
FIG. 1 shows the schematic of an experimental set-up in accordance with a preferred embodiment of the present invention.
Figure 2:
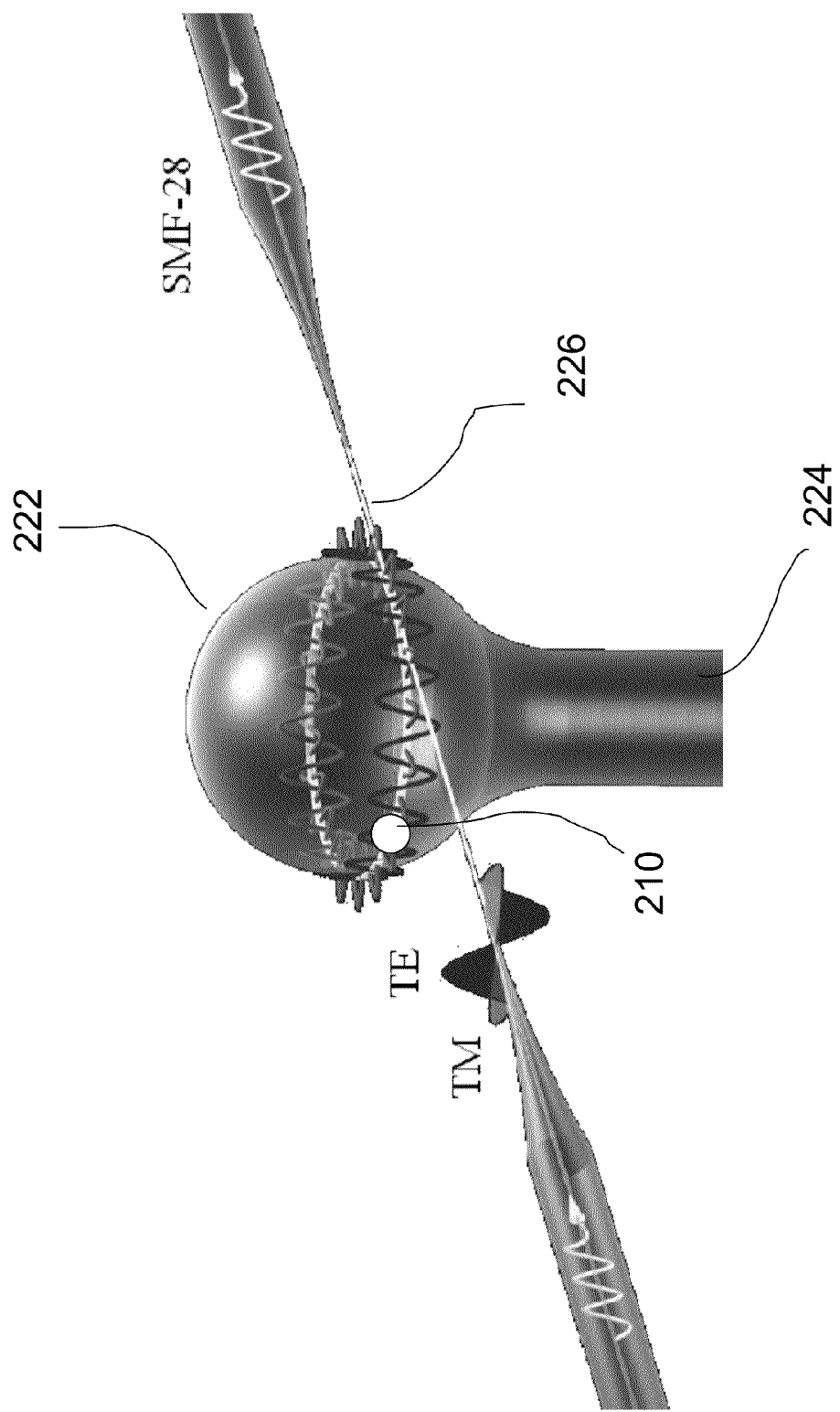
FIG. 2 illustrates how linearly polarized microcavity resonances excite and probe the molecule/particle in the direction orthogonal to (TM) or parallel with (TE) respect to the microcavity surface (xy-plane) in accordance with a preferred embodiment of the present invention.

An exemplary optical setup is described with reference to FIG. 4. A sample cell 460 was constructed by threading a single mode optical fiber (SMF-28) 442 through a 1 cm polystyrene cuvette 462. The fiber with a stripped polymer sheath was glued to the sides of the container and the exposed silica was etched with a 50% hydrofluoric (HF) acid. After a ~30-minute etch a taper 226 with a diameter of ~2-3 µm was formed, as observed with an upright microscope (not shown) equipped with a long working distance objective. The taper 226 was used to excite WGMs in optical resonators by evanescent field coupling. A silica microsphere (~300 µm diameter) 222 on-a-stem 224 was prepared by melting the tip of a SMF-28 fiber in a butane-$N_2O$ flame. It was then mounted on a mechanical stage and brought on contact with the taper 226 as shown in FIG. 2. A tunable distributed-feedback (DFB) laser diode (probe) 402 operating around $\lambda_{probe} \cong 1{,}310$ nm was coupled into the tapered fiber 442 via a fiber coupler 450. A photodiode ($PD_1$) 480 at the other end of the fiber recorded the transmission. WGMs were identified as Lorentzian-shaped troughs in a spectrum obtained by periodically tuning the DFB laser current (I) at 100 Hz with a waveform generator. The laser tuning coefficient $\Delta\lambda/\Delta I \sim 0.0055$ nm/mA was determined with a wavemeter. Spectra containing 1,000 points per scan were recorded every ~200 ms and the positions of the resonances were tracked with a computer using a LABVIEW routine based on polynomial fitting algorithm. The width (at half-maximum) of these troughs reflects the intrinsic Q-factor and absorbance of the material surrounding the cavity. A polarizer ($P_1$) 410 and a rotating half-waveplate 420 were used to selectively excite either TE or TM resonances. The polarization direction of the monitored mode was verified, using another polarizer ($P_2$) 474 and a photodiode ($PD_2$) 476, by analyzing the light scattered tangentially off the microsphere. This arrangement was used to optimize the mode coupling efficiency into to resonator by slowly etching the microsphere and the fiber with a highly diluted HF solution (<1%). The process was terminated when the probe was critically coupled into the cavity, i.e. when almost no light was transmitted on resonance, at which point the sample cell was rinsed and filled with a 10 mM phosphate buffered saline (PBS) solution (pH=7.4). Another semiconductor laser (pump) 404 emitting at $\lambda_{pump} \cong 532$ nm was coupled into the same tapered fiber 226. This green pump 404 was used to trigger photoinduced structural changes in bR which was later adsorbed onto the surface of the silica microsphere.

Figure 3:
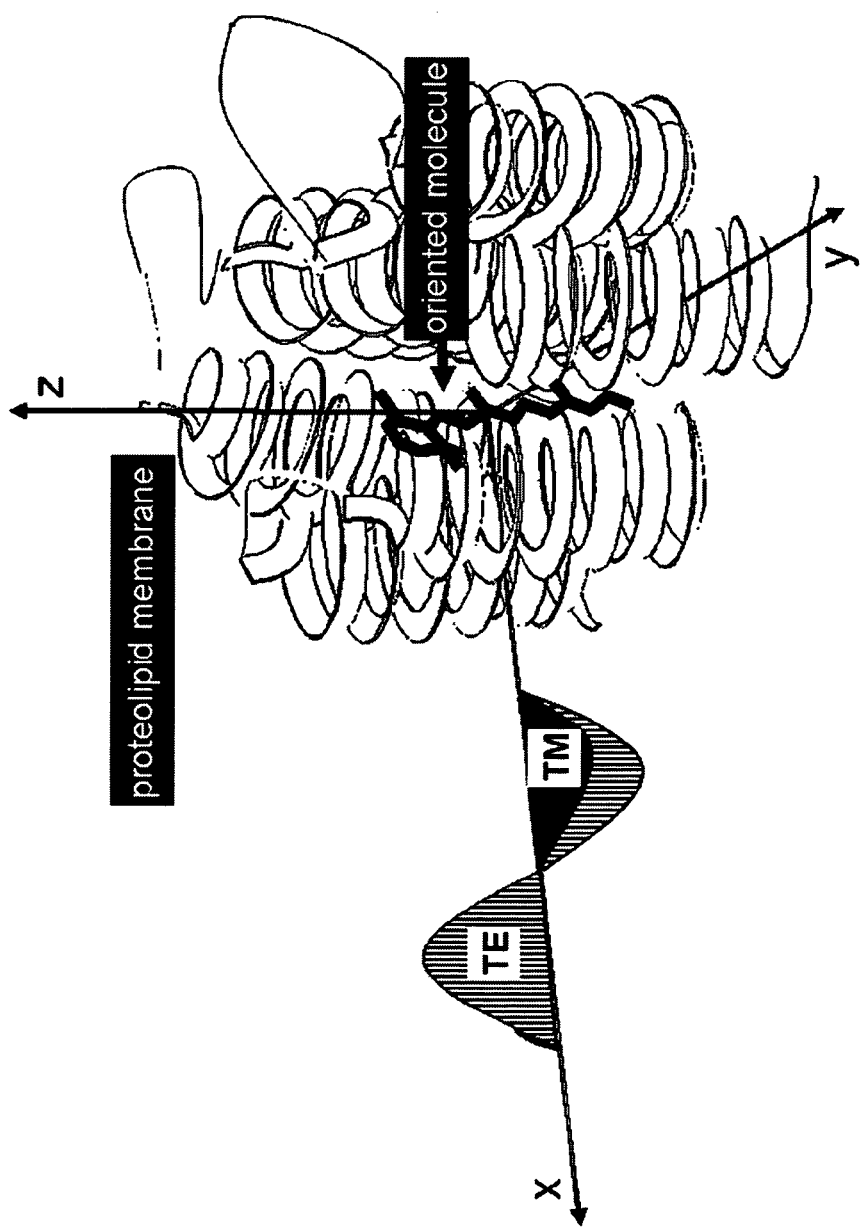
FIG. 3 illustrates a 3D ribbon-model of seven transmembrane α-helixes (white) representing the structure of bR protein embedded in a lipid bilayer (not shown) with a covalently bound all-trans retinal chromophore (black).

Method: Bacteriorhodopsin Adsorption bR forms a 5 nm-thick membrane with a well defined surface density of monomers. Blaurock, A. E., and D. Stoeckenius, "Structure of purple membrane," Nature New Biol. 233:152-154 (1971). Each monomer contains a retinal chromophore surrounded by a seven-α-helix trans-membrane protein which is embedded in a lipid bilayer composed of ten Haloarchaeal lipids per bR monomer (FIG. 3). The retinal is covalently bound to Lys216 residue via a protonated Schiff base (SB) at a fixed angle relative to the proteolipid membrane. bR thin-film formation on solid surfaces has been widely studied in the context of fabrication of optoelectronic devices and various techniques for controlled immobilization of oriented monolayers have been demonstrated. In our study we used the electrostatic deposition of bR onto a PDAC-coated silica microsphere, which was optimized for a monolayer formation. The microsphere was sonicated for 15 minutes in 350 mM solution of KOH after which a positively charged polymer poly(dimethyldiallyl)ammoniumchloride (PDAC) was pre-adsorbed onto its surface to promote successive binding of the negatively charged bR membranes. This was done by exposing the sphere to a 2% PDAC solution in 0.5 M NaCl at a pH of 6.8 for 2 minutes. The sphere was then rinsed in distilled water for additional 2 min. The bR layer was formed in situ using 1 mg/ml sonicated stock solution of D96N bR mutant (Munich Innovative Biosystems) in Milli-Q water which was further diluted (molar ratio 1:10) upon injection into the sample cell filled with PBS.

Monolayer Formation

Figure 5:
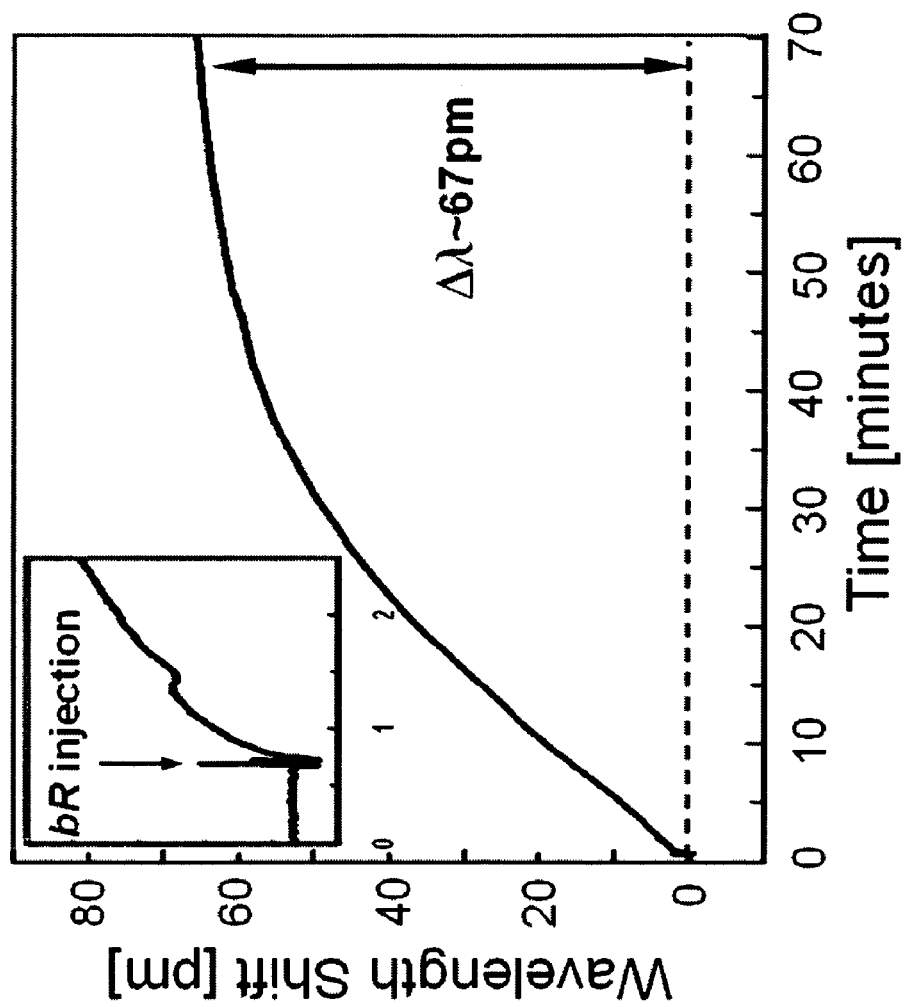
FIG. 5 is a time trace of a TM-polarized resonance wavelength shift due to bR adsorption from a liquid solution that surrounds the microcavity. The measured resonant shift at saturation, $\Delta\lambda \cong 67$ pm, points to self-assembly of a bR monolayer.

The bR adsorption process was monitored by tracking the resonant wavelength shift of a TM mode. The time-trace of the shift shows Langmuir-like adsorption kinetics which points to self-assembly of a single layer at saturation (FIG. 5). The absorption trace can be fit well by: $\Delta\lambda=\Delta\lambda_{sat}(1-e^{-t/\tau})$, where $\Delta\lambda_{sat}\cong 67$ pm is the wavelength shift at saturation and $\tau\approx 33$ min. Adsorption of the ultra-thin oriented bR layer does not significantly degrade the cavity Q which remains in the $10^6$ range. The monolayer formation is further confirmed by estimating the surface density of bR monomers, $\sigma_{bR}$, in the adsorbed layer which can be extracted from the resonant shift:

$$\sigma_{bR} \approx \left(\frac{\Delta\lambda}{\lambda}\right)\frac{\varepsilon_0(n_s^2-n_m^2)R}{\alpha_{bR}}, \quad (1)$$

where $\Delta\lambda/\lambda$ is the fractional resonant wavelength shift at saturation, R is the microsphere radius, $\alpha_{bR}$ is the molecular polarizability in excess to that of the displaced water, and $n_s$ and $n_m$ are the refractive indices of the sphere (1.47) and the PBS solution (1.33), respectively. (See S. Arnold, M. Khoshsima, I. Teraoka, S. Holler, F. Vollmer, Opt. Lett. 28, 272 (2003).). The total excess polarizability of one bR monomer for a TM mode $a_{bR}$ is the sum of the protein ($\alpha_P$), the lipids ($\alpha_L$), and the retinal ($\alpha_R$) contributions: $\alpha_{bR}=\alpha_P+\alpha_L+\alpha_R=1.05\times10^4$ au+$5.73\times10^3$ au+160 au≈$1.64\times10^4$ au (~2.4×$10^3$ Å$^3$) (See Z. Salamon, G. Tollin, Biophys. J. 80, 1557 (2001); H. M. Lee, J. Kim, C.-J. Kim, K. S. Kim, J. Chem. Phys. 116, 6549 (2002); and M. Noto, M. Khoshsima, D. Keng, I. Teraoka, V. Kolchenko, S. Arnold, Appl. Phys. Lett. 87, 223901 (2005).) Summing up the individual contributions we can use Eq. 1 to evaluate $\sigma_{bR}$. The obtained value of $9.8\times10^{12}$ cm$^{-2}$ is somewhat higher than the reported bR surface density in a monolayer ($9.12\times10^{12}$ cm$^{-2}$) determined from X-ray scattering measurements (See A. E. Blaurock, D. Stoeckenius, Nature New Biol. 233, 152 (1971).) This indicates that our self-assembly procedure yields a high surface coverage with slightly overlapping bR fragments, in agreement with observations reported in literature.

Molecular Structural Changes

Illumination of bR around 568 nm triggers a complex photocycle that contains spectroscopically different intermediaries J, K, L, M, N, and O. Throughout the photocycle, the chromophore retinal changes its conformation between the all-trans, 15-anti protonated SB found in the thermodynamically stable ground state; and the 13-cis, 15-anti deprotonated SB prevalent in the metastable M state. The bR absorption peak shifts from 568 nm to 412 nm in the process of the ground to M state transformation. In the absence of the photoexcitation, M-state relaxes spontaneously into the thermodynamically stable ground state through N and O intermediaries. The use of D96N mutant with an extended M state lifetime ensures complete conversion of bR to M-state. (See, Zeisel, D. and N. Hampp., "Spectral relationship of light-induced refractive index and absorption changes in bacteriorhodopsin films containing wild type BR$_{WT}$ and the variant BR$_{D96N}$," J. Phys. Chem. 96:7788-7792 (1992).)

The spectral shift of the bR absorption maxima due to the photochemical transformation has been shown to cause significant refractive index changes ($\Delta n$) of bR films. This is especially the case with D96N in which $\Delta n$ is about four times larger than in the wild type bR. Wavelength-dependent measurements of the index changes $\Delta n(\lambda)$ performed on bR films show a distinct maximum near the ground state absorption band at slightly larger wavelength, and the index change is progressively smaller at longer wavelengths where bR is increasingly transparent. See, Ormos, P., L. Fábián, L. Oroszi, E. K. Wolf, J. J. Ramsden, and A. Dér, "Protein-based integrated optical switching and modulation," Appl. Phys. Lett. 80:4060-4062 (2002). More specifically, the maximum index change recorded around 633 nm is $\Delta n \cong -4\times10^3$ while at 800 nm it is only $\Delta n \cong -1\times10^{-3}$. The large measured index change at 633 nm has been exploited for all-optical modulation in a novel integrable component based on OWLS technique but, to our knowledge, the possibility to probe bR far from its electronic transitions has not been explored. See, Ormos, P., L. Fábián, L. Oroszi, E. K. Wolf, J. J. Ramsden, and A. Dér, "Protein-based integrated optical switching and modulation," Appl. Phys. Lett. 80:4060-4062 (2002).

Figure 4:
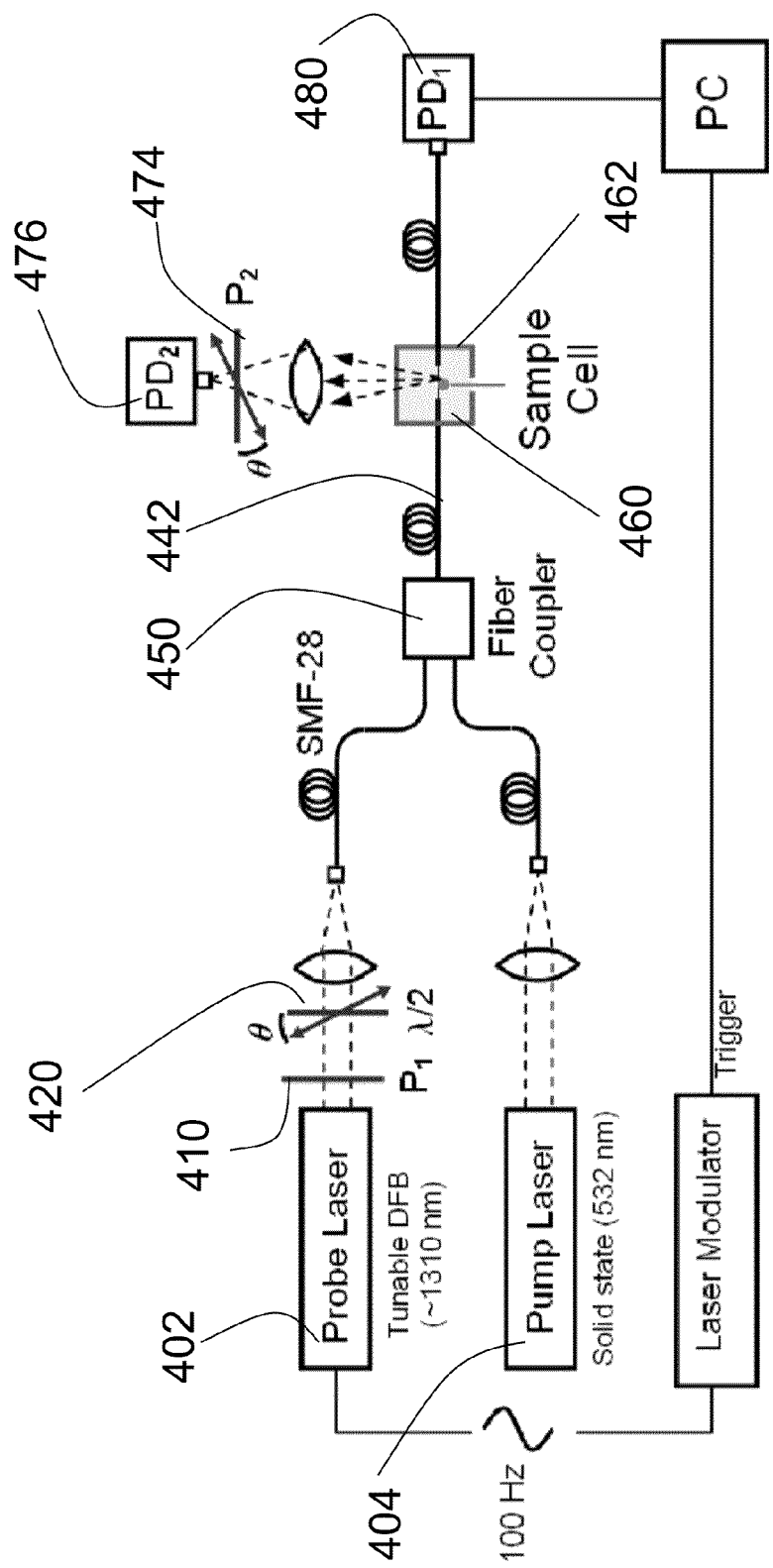
FIG. 4 illustrates an exemplary optical measurement set-up in accordance with a preferred embodiment of the present invention. $P_1$, $P_2$, polarizers; $\lambda/2$, half-waveplate; $PD_1$, $PD_2$, near-IR photodiodes; PC, personal computer for data acquisition and analysis.

In our measurements the state of the bR is controlled with a low power (<200 µW), continuous wave, green pump laser coupled to the microsphere cavity using the tapered fiber (FIG. 2, FIG. 4). The visible pump evanescently excites WGMs propagating around the microsphere's equator inducing the ground to M state conversion along their path (FIG. 2, FIG. 3). At the same time, a near-IR beam ($\lambda_{probe}\cong1,310$ nm) excites the probing resonances. The approximate bulk index change upon isomerization at the probing wavelength is only ~$-8\times10^{-4}$, as extrapolated from the Kramers-Kronig transformation of the published absorption data. The photoexcitation of the retinal reduces the refractive index of bR which causes a negative shift of the TE and TM resonances (FIG. 6). bR forms an anisotropic, ultra-thin macromolecular monolayer on the cavity surface where the evanescent field intensity is the highest. Although only a small fraction of the evanescent tail interacts with the bR membranes, we are sensitively probing molecular changes in a highly oriented anisotropic system. We therefore choose polarizability rather than refractive index to describe the photochromic transitions. Given the measured surface density of bR monomers, Eq. 1 can be used to calculate the average polarizability change at $\lambda_{probe}$ of a single bR molecule upon photoexcitation:

$$\langle \Delta \alpha_{avg} \rangle = \frac{1}{3}(\langle \Delta \alpha_{TM} \rangle + 2 \langle \Delta \alpha_{TE} \rangle)$$

$$= -384 \text{ au}(\sim -57 \text{ Å}^3).$$

The value reflects structural changes of the retinal in its complex proteolipid environment. On the molecular level, the measured shifts of resonances are caused by the change of the retinal polarizability tensor and the related conformational changes in the surrounding protein. Our experiments show that off-resonant monitoring of structural changes and anisotropies in optically active materials is possible with high-Q optical microcavities, even when the changes occur in optically dilute molecular monolayers.

To test the validity of the introduced method, we compare the polarizability change $\langle \Delta \alpha_{avg}(1310 \text{ nm})\rangle$ to the corresponding polarizability and index changes measured in bR thin-films with the established optical techniques (See, Zeisel, D. and N. Hampp., "Spectral relationship of light-induced refractive index and absorption changes in bacteriorhodopsin films containing wild type $BR_{WT}$ and the variant $BR_{D96N}$," J. Phys. Chem. 96:7788-7792 (1992).)

Since $\Delta n$ depends on the optical density (OD) and pH of the bR film, we use published results obtained on a film with a moderate OD of 3.6 and pH of 8 in which the maximum measured refractive index change was $\Delta n(633 \text{ nm}) \cong -4 \times 10^{-3}$. The Lorenz-Lorentz formula was applied to express the refractive index change as the change of the molar refraction $\Delta R = R_M - R_{ground} = -3.6 \times 10^{-22}$ cm$^3$ molecule$^{-1}$. Using the standard definition of molar refraction:

$$R(\lambda) = \frac{4\pi}{3} N_A \alpha(\lambda),$$

where $N_A$ in the Avogadro's constant, we obtain the corresponding change of the molecular polarizability of a single bR monomer $\Delta \alpha(633 \text{ nm}) \cong -580$ au ($-86$ Å$^3$). Since the probing wavelength is within the absorption band of the ground state, the result is an approximate lower limit of the polarizability change. As expected, the absolute value is larger than the one we measured with WGMs far from the absorption band at 1,310 nm.

Time Response Study

Figure 7:
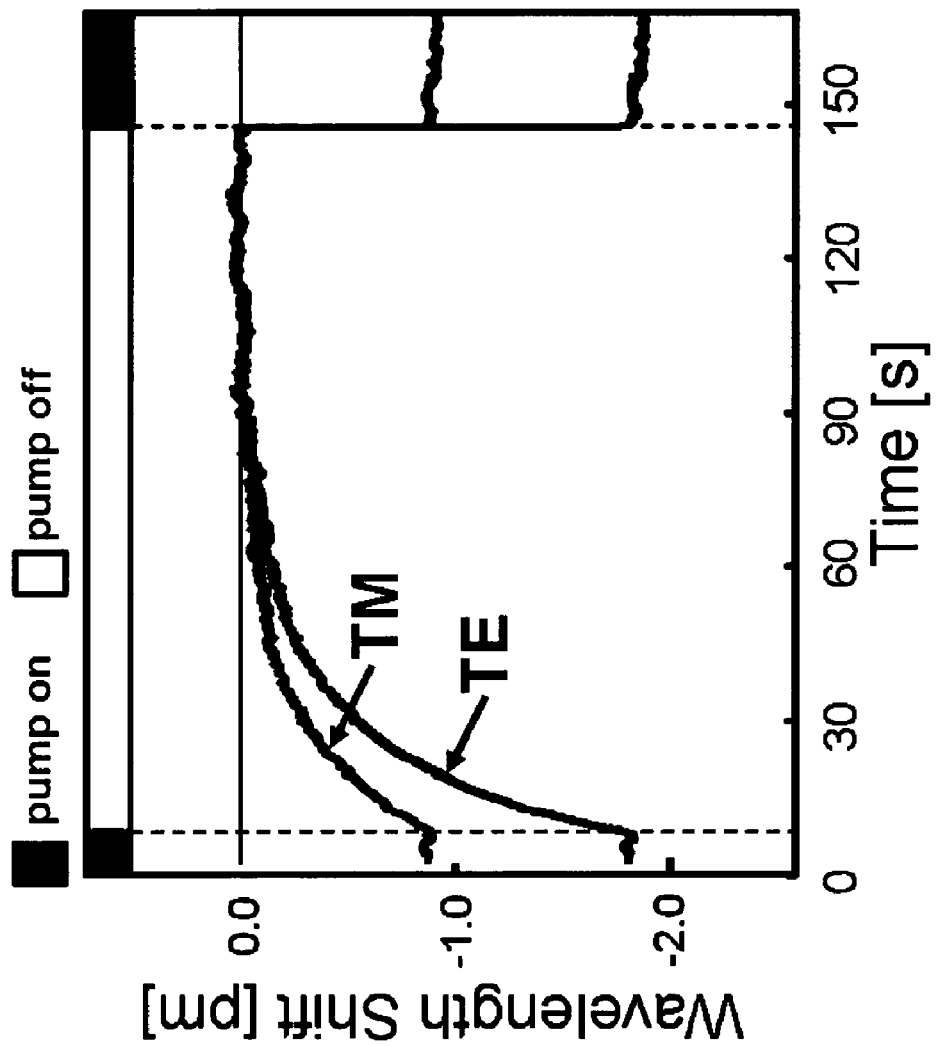
FIG. 7 illustrates dynamics of the ground to M state transformation observed by tracking wavelength shifts of TE- and TM-polarized microcavity modes.

Time-resolved switching data for a step modulation of a low-intensity, continuous wave pump is presented in FIG. 7. Since the intensity of the pump is resonantly enhanced by recirculation in the microcavity, moderate pump powers (<200 μW) are sufficient to fully photoexcite bR molecules. The time traces of near-IR resonant wavelength positions for two polarizations reveal a fast timescale associated with the photoinduced M state buildup and a slow thermal relaxation into the ground state at $\tau \sim 11$ s. The results are consistent with the timescales of photochromic transformations of D96N. In the absence of pulsed excitation and triggered, high-speed data acquisition, faster transition timescales corresponding to the transient intermediaries J, K, L, N and O were not resolved in our measurements. In principle, microcavities can monitor molecular processes in real time if their timescales are longer than the cavity photon lifetime, $$\tau_{cav} = \frac{Q}{2\pi v},$$

where Q is the cavity quality factor, and v is the frequency of the probing light. With $Q\sim 10^6$ and $v\sim 2\times 10^{14}$ Hz, silica microspheres should be able to dynamically resolve nanosecond transitions and quantify molecular polarizabilities of the corresponding intermediaries.

Retinal Orientation

Figure 6:
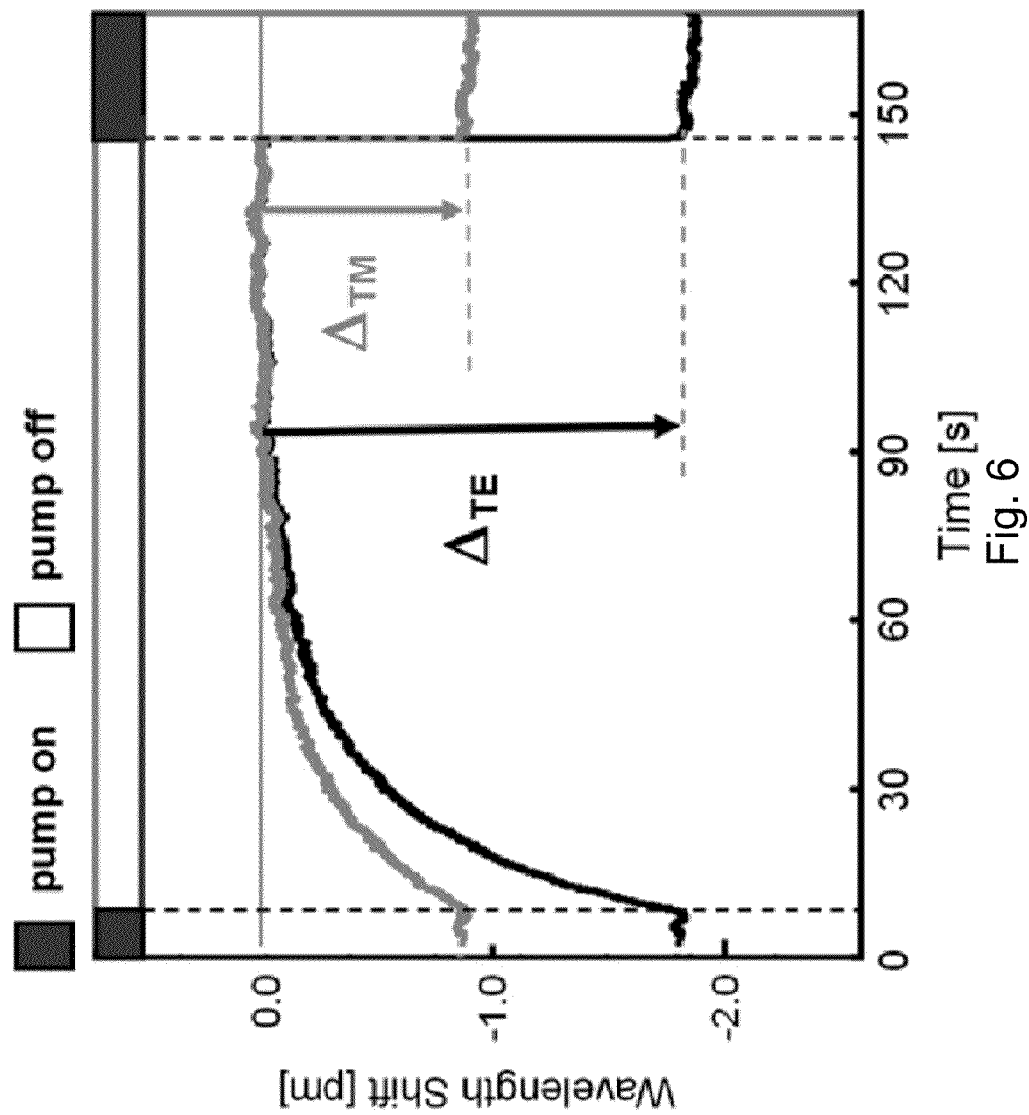
FIG. 6 is a transmission spectra for a TE and a TM polarized WGM. A negative resonance wavelength shift is observed upon photoexcitation of the adsorbed bR monolayer. The shift is about twice as large for the TE than for the TM mode, which is due to the retinal orientation in the bR membrane.
Figure 8:
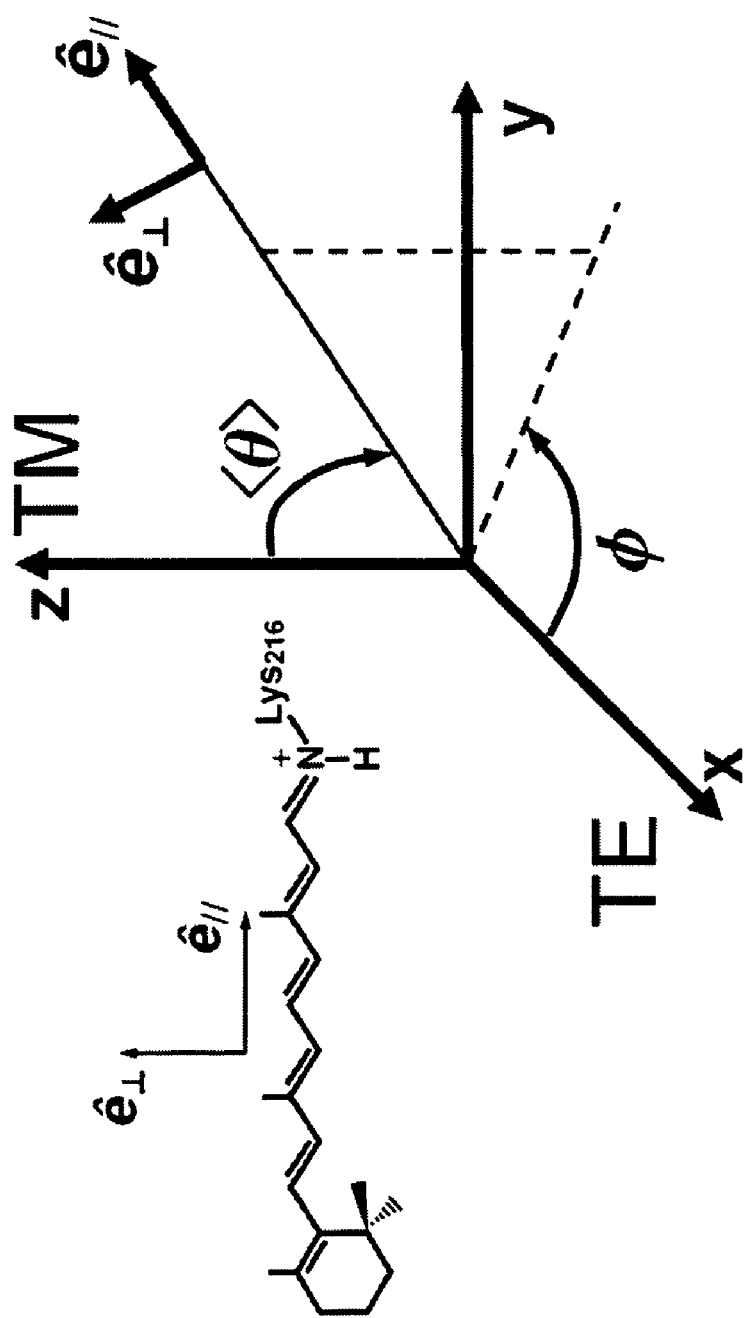
FIG. 8 illustrates angles defining the average orientation of the retinal relative to the polarization direction of the probing resonances.

We have consistently observed the shift ratio for the TE and TM polarizations ($\Delta\lambda_{TE}/\Delta\lambda_{TM}$) of $2.1\pm 0.1$ (FIG. 6). This, as we are going to show, can be directly related to the orientation of the retinal relative to the bR membrane. We define the orientation angle $\Phi$ as the angle between the membrane normal and the $C_5$-$C_{13}$ bond in the retinal (FIG. 8). Retinal isomerization changes the dipole moment induced by the evanescent field of the optical resonance. This causes a change of the photon energy of the single photon resonant state, which shifts the resonant frequency ω by:

$$\hbar \delta \omega \approx -\frac{1}{2} \vec{E}(\vec{r}, t) \cdot \delta \hat{\alpha} \cdot \vec{E}^*(\vec{r}, t) \quad (2)$$

where $\vec{E}(\vec{r}, t)$ is the electric-field vector of the probing mode and $\delta\hat{\alpha}$ is the tensor describing the polarizability change. In our analysis we consider the retinal as rod-like molecule undergoing changes of the molecular polarizability $\delta\alpha_\parallel$ and $\delta\alpha_\perp$ along the major retinal axis ($\hat{e}_\parallel$) and perpendicular to it ($\hat{e}_\perp$), respectively. We ignore the slight rotation of the retinal polarizability axis caused by the structural transformation, and consider the molecule to be oriented at a fixed average angle $\langle \theta \rangle$ from the membrane plane normal (z) (FIG. 3). We use the longitudinal $\langle \theta \rangle$ and the azimuthal angle φ to define the orientation of the retinal with respect to the polarization directions of the resonant modes oriented along the x- (TE) and z-axis (TM). For the TM mode, $\langle \theta \rangle$ is constant for all possible in-plane orientations of the retinal. The fractional wavelength shift for TM modes upon retinal isomerization can be expressed in terms of $\langle \theta \rangle$ and the changes of molecular polarizabilities $\delta\alpha_\parallel$ and $\delta\alpha_\perp$ as:

$$\frac{\Delta\lambda_{TM}}{\lambda} \approx (\delta\alpha_\perp \sin^2\langle\theta\rangle + \delta\alpha_{//}\cos^2\langle\theta\rangle)\frac{|E_{TM}|^2}{2E_0} \quad (3)$$

Here $|E_{TM}|^2$ is the average field amplitude of the TM mode at the resonator surface and $E_0 = \int \in_s |\vec{E}(\vec{r})|^2 dV$ is the total electromagnetic mode energy contained in the interior of the microsphere with permittivity $\in_s$.

For the TE polarization the angle between the polarization direction (x) and the molecular axis varies with the retinal in-plane orientation represented by the azimuthal angle φ. Averaging this over all possible angles φ to account for contributions of retinals randomly oriented in the membrane plane we obtain:

$$\frac{\Delta\lambda_{TE}}{\lambda} \approx \frac{1}{2}[\delta\alpha_\perp(1 + \cos^2\langle\theta\rangle) + \delta\alpha_{//}\sin^2\langle\theta\rangle]\frac{|E_{TE}|^2}{2E_0} \quad (4)$$

The ratio of the resonant shifts for the TE and TM polarizations then becomes:

$$\frac{\Delta\lambda_{TE}}{\Delta\lambda_{TM}} \approx \frac{1}{2}\left[\frac{\delta\alpha_\perp(1+\cos^2\langle\theta\rangle)+\delta\alpha_{//}\sin^2\langle\theta\rangle}{\delta\alpha_\perp\sin^2\langle\theta\rangle+\delta\alpha_{//}\cos^2\langle\theta\rangle}\right]\frac{|E_{TE}|^2}{|E_{TM}|^2} \quad (5)$$

To simplify this equation further we assume equal amplitudes of TE and TM whispering gallery modes, i.e. $|E_{TE}|^2 \approx |E_{TM}|^2$; $\langle\theta\rangle$ is related to the wavelength shift ratio of TE and TM modes upon retinal isomerization by:

$$\frac{\Delta\lambda_{TE}}{\Delta\lambda_{TM}} \approx \frac{1}{2}\left(\frac{1+\cos^2\langle\theta\rangle+\beta\sin^2\langle\theta\rangle}{\sin^2\langle\theta\rangle+\beta\cos^2\langle\theta\rangle}\right). \quad (6)$$

Here $\beta$ denotes the ratio of the photoinduced changes in $\alpha$ along and perpendicular to the major molecular axis which we define here along the $C_5$-$C_{13}$ bond; $\beta=\delta\alpha_{//}/\delta\alpha_\perp$. According to the result of ab initio calculations of $\alpha$ $|\delta\alpha_{//}|$ is an order of magnitude lager than $|\delta\alpha\perp|$, and therefore $\beta \approx -10$. The value is negative because the trans-cis isomerization of $C_{13}$-$C_{14}$ bond causes the polarizability to decrease along the major molecular axis and increase perpendicular to it. As it is difficult to numerically study the full bR membrane structure with all of its proteolipid components only the chromophore retinal has been considered in these tentative calculations. The results for the retinal orientation are relatively insensitive to the precision of $\beta$-values used in the calculation. The measured value of $\Delta\lambda_{TE}/\Delta\lambda_{TM}$ corresponds to $\langle\theta\rangle$ of ~61°. It is interesting to compare this result to measured retinal orientations obtained with alternative methods. The value is in excellent agreement with the reported average angle obtained with 3D X-ray diffraction; $\langle\theta\rangle \cong 60.7°$. It is however considerably smaller than the orientation angle of the optical transition dipole that has been measured at 69.0° in the ground and at 66.9° in the M state, i.e. $\langle\theta\rangle \cong 68°$. See, Heyn, M. P., B. Borucki, and H. Otto., "Chromophore reorientation during the photocycle of bacteriorhodopsin: experimental methods and functional significance," Biochimica et Biophysica Acta 1460:60-74 (2000). The experiments in the present form do not provide direct means to determine orientation of the transition dipole. The dipole axis is not aligned with the $C_5$-$C_{13}$ bond, but its orientation can be investigated experimentally with microspheres by controlling the polarization direction of the pump. Different excitation efficiencies for TE- and TM-polarizations would reveal the orientation of the optical transition dipole. It should be noted that, since we assumed axial symmetry of the retinal and disregarded the slight change of $\theta$ upon photoexcitation in the derivation of Eq. 6, and used an approximate computed value of $\beta$ to get $\langle\theta\rangle$, the excellent agreement with the high-resolution structural data might be somewhat fortuitous. Nevertheless, our experiments seem to indicate that orthogonally polarized resonant modes in silica microspheres can non-invasively probe optical anisotropies in molecular monolayers. Finally, we also want to emphasize that the technique described herein cannot distinguish between the two possible binding bR membrane orientations, i.e. they cannot determine the respective fractions of bR fragments bound to the surface with its cytoplasmic and extracellular side. This however has no bearing on the conclusions regarding the polarizability values and the retinal orientations.

Sensitivity Estimate

We would like to comment on the sensitivity of our technique and its applicability to measurements of the polarizability and its anisotropies in molecular systems, particularly those that absorb visible light. A typical silica microsphere (Q~$10^6$) coated with biomolecules at a surface density of the order of $10^{13}$ cm$^{-2}$ can resolve the polarizability change ($\Delta\alpha$ of ~3 au (~0.4 Å$^3$) in the near-IR. The rough estimate assumes an experimental resolution for the resonant shift of ~$\frac{1}{50}$ of the linewidth. The sensitivity is rather remarkable considering that the polarizability of a hydrogen molecule is ~0.8 Å$^3$ and trans-cis isomerization of a single C—C bond and deprotonation can change the polarizability by hundreds of atomic units. Although conformational changes in such systems have been observed qualitatively by CPWR and indirectly by Stark spectroscopy, the magnitude of $\Delta\alpha$ that accompanies structural transformations in complex proteolipid macromolecules is not known. Given their superior sensitivity and the ability to directly quantify $\Delta\alpha$, the microresonators represent a new quantitative tool for probing molecular transformations in important proteolipid biomolecular assemblies such as G-protein-coupled receptors or in signaling molecules such as calmodulin and disease-related prion proteins. As shown herein for the model case of bR, the introduced technique is particularly suited for off-resonant pump-probe studies of photosensitive biomolecules. Further examples of such systems include photosynthetic membranes and photoreceptors such as photoactive yellow protein. The latter can also be used as photochromic labels in fusion proteins to study molecular processes and anisotropies imposed by their e.g. proteolipid environment. Most importantly however, further improvements of the microresonator technique promise single-molecule sensitivity which is beyond the scope of any alternative label-free technique.

Please also refer to provisional application for United States Letters Patent of Frank Vollmer and Juraj Topolancik for "Methods, Materials and Devices for Light Manipulation with oriented Molecular Assemblies in Micronscale Photonic Circuit Elements with High-Q or Slow Light" U.S. Patent Application Publication No. 20090136181.

Example of a Setup that Uses Microcavities in Photonic Crystal Slabs

High-refractive-index slabs with 2D arrays of air-holes exhibit large PBGs for the TE-like polarization (FIG. 9) (E-field parallel to 2D-plane) (T. Krauss, R. DeLaRue, and S. Brand, Nature 383, 699 (1996)), which established them as a popular platform for designing waveguides (M. Loncar et al., J. Lightwave Technol. 18, 1402, (2000), S. G. Johnson et al., Phys. Rev. B, 62, 8212 (2000), M. Notomi et al., Phys. Rev. Lett. 87, 253902 (2001)), and nanocavities (O. Painter, J. Vučković, and A. Scherer, J. Opt. Soc. Am. B 16, 275 (1999), Y. Akahane et al., Nature 425, 944 (2003), H.-G. Park et al., Appl. Phys. Lett. 79, 3032 (2001)). Engineered PhC nanostructures guide and confine light remarkably well by relying on Bragg reflections in the 2D-plane and on total internal reflection in the out-of-plane direction. Guiding losses and cavity quality (Q) factors are believed to be limited primarily by the fabrication-induced surface roughness which breaks the PhC periodicity and destroys the Bloch-wave coherence by diffusive scattering. Considerable efforts have thus been expended to improve fabrication processes which, together with the progress in design optimization, have produced highly-dispersive (or slow-light) waveguides (H. Gersen et al., Phys. Rev. Lett. 94, 073903-1 (2005), Y. A. Vlasov et al., Nature 438, 65 (2005)), and optical nanocavities with ultra-high Qs and record-low modal volumes (B.-S. Song et al., Nature 4, 207 (2005)).

Figure 9:
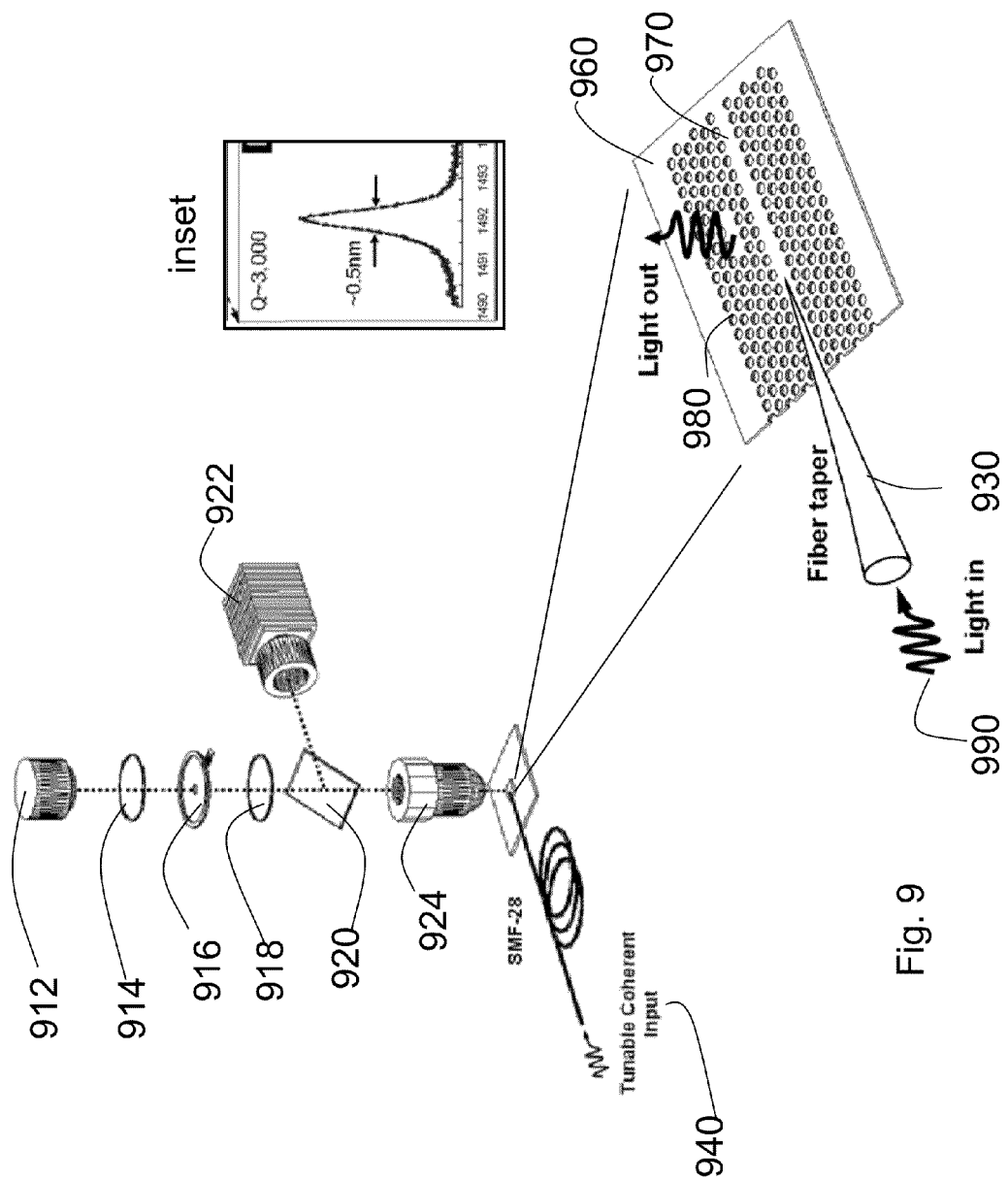
FIG. 9 is a schematic diagram of the measurement setup used in one preferred embodiment of the present invention. Vertically scattered light from a photonic crystal slab (PhC) is collected with an objective (O) and imaged with a lens (L1) onto a field-stop (FS) consisting of a variable aperture which restricts analysis of scattered light to a certain area on the PhC slab. Another lens (L2) re-focuses light from the selected area into an IR photodiode (PD). A beam splitter redirects a fraction of the collimated beam into an IR charge coupled device camera (IR-CCD) for imaging. Inset shows example of a (scattering) spectrum for a high-Q cavity. A tapered fiber tip is used to couple light to the photonic crystal structure.

FIG. 9: Coherent light 990 from an infrared (IR) diode laser 940 tunable from 1,475 to 1,580 nm, was coupled into waveguide 970 (W1s) from a single-mode optical fiber (SMF-28). To compensate for the significant impedance mismatch inherent to conventional end-fire coupling, PhC modes were excited with a non-linear fiber taper 930. The taper, prepared by pulling a melted fiber and etching its tip down to the W1 dimensions ($\sqrt{3} \times a$), was positioned on top of the PhC-slab 960 as illustrated in FIG. 9. The arrangement allows the light to leak out of the taper 930 and to evanescently couple into W1 970. Once excited, the PhC modes propagate in the waveguide 970 and interact with cavities 980 which leak the light vertically out of the slab. This light was collected with an infinity-corrected objective 924 (100, NA=0.80) and its intensity monitored with an InGaAs photodiode 912 as the coherent source was scanned. A beamsplitter 920 redirected a fraction of the collimated beam to an IR camera 922 for imaging. A field stop 916 was placed in front of the photodiode to locally probe 10 μm-long waveguide sections and to block parts of the free-propagating beam deflected accidentally into the objective from surface impurities. An arrangement of lenses 914 and 918 focuses the light on the photodetector 912. A typical scattering spectrum of the high Q-cavity is shown in the inset of FIG. 9. The photonic crystal cavity can be used in similar fashion as a microsphere cavity to implement pump-probe spectroscopy by coupling several beams to the waveguide-microcavity system. Furthermore, a disordered waveguide operated in the slow-light regime can be used in similar fashion. Please refer to provisional application for United States Letters Patent of Frank Vollmer and Juraj Topolancik for "System and Methods for Strong Photon Localization in disordered photonic crystal waveguides," U.S. Patent Application Publication No. 20100176200.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. An optical device comprising:
 a high-Q resonant structure;
 one of an interface, a surface and a mode volume accessible for interactions with a sample; and
 means for simultaneously exciting resonant modes in said high-Q structure at one or more pump wavelengths and at one or more probe wavelengths;
 wherein said means for exciting comprises a pump laser and a probe laser coupled to said high-Q resonant structure, wherein said pump laser causes perturbations of molecules adsorbed on said high-Q resonant structure and said probe laser measures said perturbations.

2. An optical device according to claim 1, wherein said high Q structure comprises at least one selected from the group of: microspherical cavities, microtoroidal cavities, microring-cavities, microdisk cavities, photonic crystal defect cavities, disordered photonic crystal waveguides, fabry-perot cavities, photonic crystal waveguides, donor-type photonic crystal cavities, and acceptor-type photonic crystal cavities.

3. An optical device according to claim 1, wherein said resonant modes are linearly or circularly polarized.

4. An optical device according to claim 1, wherein said resonant modes are excited by one of evanescent coupling from an optical waveguide, evanescent coupling from a photonic crystal waveguide, evanescent coupling from a tapered optical fiber, evanescent coupling from a tapered optical fiber tip, and coupling from a free-space beam.

5. An optical device according to claim 4, wherein said tapered fiber tip is prepared by pulling and chemical etching of a single mode optical fiber.

6. An optical device according to claim 1, wherein said resonant modes are excited using at least one selected from the group of: distributed feedback laser, an external cavity laser, an organic dye laser, surface emitting laser diodes, and quantum dot emitters.

7. An optical device according to claim 1, wherein a wavelength of a resonant mode is detected from spectral features of a transmission or scattering spectra recorded with photodiodes in a spectral regions.

8. An optical device according to claim 1, wherein transfer characteristics of said high Q structure are determined from intensity measurements of transmitted or scattered light recorded with photodiodes in one or more spectral regions.

9. A device according to claim 1, wherein said sample is delivered to said volume using pressure operated microfluidic channels or microfluidic channels operated by electrophoresis, dieelectrophoresis, or where optical force is used to accumulate the sample in the sensor region.

10. A device according to claim 1, wherein said sample self assembles on the said interface or surface.

11. A device according to claim 1, wherein said sample comprises one of a liquid, a gas, a molecular monolayer, a self-assembled monolayer, an ultra-thin film, un-specifically adsorbed protein molecules, un-specifically adsorbed DNA molecules, specifically bound protein molecules, specifically bound DNA molecules, small organic molecules, antibodies, and a single molecule.

12. A method for measuring optical polarizability and its anisotropy which uses a probe, the method comprising the steps of:
 measuring a baseline transmission spectrum with a device according to claim 1, where spectral features are used to determine one or more resonant wavelengths and/or linewidths and/or transfer characteristics for one or more resonant or waveguide modes excited by a probe beam;
 exposure of the device according to claim 1 to said sample;
 measuring transmission spectra to determine one of changes in resonant wavelengths, linewidths and transfer characteristics for one or more resonant or waveguide modes;
 determining one of the average polarizability or anisotropy of a sample based on a wavelength shift or change in transfer characteristics measured for one or more differently polarized resonant or waveguide modes, the extinction coefficient or scattering cross section of a sample based on the linewidth change measured for one or more resonant or waveguide modes and the molecular orientation or conformational state or anisotropy of a sample based on wavelengths shifts measured for differently polarized resonant or waveguide modes.

13. A method according to claim 12, further comprising the step of:
   inducing a polarizability or hyperpolarizability or conformational change or a change in chemical structure in said sample using a chemical, physical or biological perturbation.

14. A method according to claim 13, wherein said perturbations are induced by one or more of the following: a laser pulse, a cw laser, an applied electric field, an electric field applied across a membrane, an electric field due to intrinsic charges of molecules, variation of temperature, variation of pressure, variation of pH, exposure to chemicals, binding of molecules, conformational molecular changes, reorientation of molecules, self-assembly of molecules, folding and unfolding of protein molecules, binding of low molecular weight compounds, induced Kerr- or Pockels effects, induced membrane potentials, induced action potentials in nerve cells, changes in concentration of chemicals such as ions, changes in osmotic pressure, or changes in osmolarity.

15. A pump probe method using a device according to claim 1, comprising the step of exciting the resonant or waveguide modes at a pump wavelength that overlaps with an absorption line in said sample; and wherein said probe wavelength is chosen to maximize Q-factor in the resonant cavity or minimize group velocity in said slow light structure.

16. An optical device according to claim 1, wherein the pump triggers conformational changes, breaks/forms chemical bonds, induces excited states, excites vibrational and rotational modes, induces/prevents chemical reactions, generates heat by absorption in molecules bound to said microcavity interface or surface, or in molecules dispersed in said modal volume of the resonant mode.

17. A pump probe method in optical devices comprising the steps of:
   exciting optical resonances in a high-Q structure at one or more pump wavelengths at a specific state of polarization and at an intensity;
   simultaneously exciting optical resonances in said high-Q structure at one or more probe wavelengths different from the pump wavelength and at specific state of polarization and at an intensity;
   measuring a transmission spectra or scattering spectra or measurement of transfer characteristics of one or more probe beams through the high-Q structure by scanning the wavelength of one or more pump beams, or by changing the state of polarization of one or more pump beams, or by changing the intensity of one or more pump beams, or by changing the state of polarization of one or more probe beams, or by scanning the wavelength of one or more probe beams.

18. A pump-probe method according to claim 17, wherein said step of measuring a transmission spectra or scattering spectra or measurements of transfer characteristics comprises calculating one of a polarizability change in a sample interacting with the optical device, an anisotropy of a sample interacting with the optical device, an orientation of a sample interacting with the optical device, an absorption cross section of a sample interacting with the optical device, and a refractive index change of a sample interacting with the optical device.

19. A pump-probe method according to claim 17, wherein said measurements of transmission spectra or scattering spectra or measurements of transfer characteristics are used to detect a particle binding to the optical device by performing one of the following steps:
   varying intensity of one or more pump beams before and after interaction of the particle with the optical device and monitoring associated changes in the transfer characteristics/changes in transmission spectra/changes in scattering spectra;
   varying the state of polarization of one or more pump beams before and after interaction of the particle with the optical device and monitoring associated changes in the transfer characteristics/changes in transmission spectra/changes in scattering spectra;
   varying wavelength of one or more pump beams before and after interaction of the particle with the optical device and monitoring associated changes in the transfer characteristics/changes in transmission spectra/changes in scattering spectra;
   varying wavelength of one or more probe beams before and after interaction of the particle with the optical device and monitoring associated changes in the transfer characteristics/changes in transmission spectra/changes in scattering spectra; and
   varying state of polarization of one or more probe beams before and after interaction of the particle with the optical device and monitoring associated changes in the transfer characteristics/changes in transmission spectra/changes in scattering spectra.

20. A pump-probe method according to claim 19, wherein said particle comprises one of the following: a single molecule, a single macromolecule, a single protein molecule, a single DNA molecule, an aggregate of molecules, a virus, a cell, a colloidal particle, a metal particle.

* * * * *